United States Patent
Bitzer et al.

(10) Patent No.: US 9,289,263 B2
(45) Date of Patent: Mar. 22, 2016

(54) CATHETER ARRANGEMENT

(71) Applicant: VascoMed GmbH, Binzen (DE)

(72) Inventors: Andreas Bitzer, Zurich (CH); Stephan Fandrey, Affoltern am Albis (CH)

(73) Assignee: VASCOMED GMBH, Binzen (DE)

( * ) Notice: Subject to any disclaimer, the term of this patent is extended or adjusted under 35 U.S.C. 154(b) by 547 days.

(21) Appl. No.: 13/776,700

(22) Filed: Feb. 25, 2013

(65) Prior Publication Data

US 2013/0253490 A1    Sep. 26, 2013

Related U.S. Application Data

(60) Provisional application No. 61/614,547, filed on Mar. 23, 2012.

(51) Int. Cl.
| | |
|---|---|
| *A61B 18/24* | (2006.01) |
| *A61B 18/14* | (2006.01) |
| *A61B 19/00* | (2006.01) |
| *G01K 11/32* | (2006.01) |
| *G01B 11/16* | (2006.01) |
| *A61B 18/00* | (2006.01) |

(52) U.S. Cl.
CPC ............ *A61B 18/24* (2013.01); *A61B 18/1492* (2013.01); *A61B 19/46* (2013.01); *G01B 11/16* (2013.01); *G01K 11/3206* (2013.01); *A61B 2018/00791* (2013.01); *A61B 2019/465* (2013.01)

(58) Field of Classification Search
CPC .................................................... A61B 18/1492
See application file for complete search history.

(56) References Cited

U.S. PATENT DOCUMENTS

| | | |
|---|---|---|
| 5,399,854 A | 3/1995 | Dunphy et al. |
| 6,278,810 B1 | 8/2001 | Sirkis et al. |
| 2007/0060847 A1 | 3/2007 | Leo et al. |
| 2008/0285909 A1 | 11/2008 | Younge et al. |
| 2012/0220879 A1 | 8/2012 | Fandrey et al. |

FOREIGN PATENT DOCUMENTS

WO    2009/138957    11/2009

OTHER PUBLICATIONS

European Search Report issued for EP Application No. 13156972.5, dated Jul. 19, 2013, 4 pages.

*Primary Examiner* — Carl H Layno
*Assistant Examiner* — Jennifer Ghand
(74) *Attorney, Agent, or Firm* — Arc IP Law, PC; Joseph J. Mayo

(57) ABSTRACT

At least one embodiment of the invention relates to a catheter arrangement comprising a catheter with a proximal section and a distal section, to measure a force acting on the distal section and simultaneously receive a temperature signal prevailing in the distal section. According to at least one embodiment of the invention, the catheter arrangement comprises an evaluation unit connected to a single combined optical force and temperature sensor, and further comprises a readout signal generator to generate and feed a readout signal modulated with a carrier frequency into the force sensor and temperature sensor. According to at least one embodiment of the invention, the catheter arrangement comprises a first readout device to read out a first modulated measuring signal portion, a second readout means to read out a second unmodulated measuring signal portion, and a processing unit to combine the first and second measuring signal portions.

17 Claims, 4 Drawing Sheets

CATHETER ARRANGEMENT

This application claims the benefit of U.S. Provisional Patent Application 61/614,547 filed on 23 Mar. 2012, the specification of which is hereby incorporated herein by reference.

BACKGROUND OF THE INVENTION

1. Field of the Invention

At least one embodiment of the invention relates to a catheter arrangement having a catheter, in particular ablation catheter, with an optical force sensor, which is integrated in the distal section thereof and which is configured and arranged to measure an external force acting on the distal section.

2. Description of the Related Art

In certain fields of use of catheters or similar devices, e.g. electrode lines, a pressing force applied to adjacent tissue is important for the functionality of such devices, therefore detection of this contact force is of interest. This applies in particular to ablation catheters by means of which tissue areas are atrophied or tissue parts are ablated.

An example of an ablation catheter is Enclosense's "TactiCath®" that enables measuring a force acting on a distal catheter end during an ablation process in terms of amount and direction. A catheter of this type utilizes the principle of the so-called FBG (Fiber-Bragg-Grating) sensor, wherein three fibers, each with one FBG sensor at the fiber end, form a group of sensors, which is necessary for a 3D force measurement. For joint measuring signal processing, the sensors can be connected to a signal processing unit. The sensors are attached at an angular distance of 120° on the outside of a deformable cylinder.

In Patent Application Publication No. U.S. 2008/0285909 A1, the functionality of FBG sensors for determining twistings or curvatures of the catheter body, is described in detail and also the functionality of the aforementioned force sensor with a plurality of FBG fibers attached to a deformable cylinder is explained.

In International Patent Application Publication WO 2009/138957 A2, temperature compensation by means of electrical thermocouples is provided because with the FBG measurement method, even small temperature changes or deviation between the individual sensors can cause significant measurement uncertainties. Also, during an electrothermal ablation process, considerable temperature fluctuations can occur at the tip of the ablation catheter. It is also known from the mentioned printed matter to reduce the thermal conductivity between the ablation head of an ablation catheter (which can become very hot) and the force sensors in order to reduce the effect of temperature changes on the result of the force measurement. In each case, the structure of the catheter is extremely complex resulting in high production cost for the catheter itself and also for the associated evaluation unit.

The optical measurement principle of FBG sensor systems is generally known and also known in particular in connection with its use for force measurements and temperature measurements; cf., for example, www.wikipedia.org/wiki/Fiber_Bragg_grating and U.S. Pat. No. 5,399,854.

Applicant's co-pending U.S. Patent Application Publication. 20120220879 A1, discloses a catheter, a catheter arrangement and a force measuring device, wherein an individual FBG fiber fixed in a sensor holder comprises three force sensor regions that form force sensors for joint measuring signal processing, and wherein, in addition, a T sensor region can be provided on the fiber.

BRIEF SUMMARY OF THE INVENTION

It is an object of at least one embodiment of the invention to provide a catheter arrangement of the aforementioned type which is simplified in terms of its structure and also with regard to the connection to an associated signal processing unit and to signal processing, and therefore is cost-effective.

An object is achieved with a catheter arrangement having the features as claimed herein. Furthermore, a corresponding new force and attenuation measuring device is claimed and described herein. Advantageous refinements of the inventive idea are subject matter also claimed herein.

At least one embodiment of the invention is based on the consideration to dismiss the previous concept of providing an additional temperature sensor for the detection (and the subsequent compensation) of the significant temperature dependency of the force signal of an optical force sensor. Instead, one or more embodiments are directed towards using the measuring signal of the optical force sensor itself for determining relevant temperature changes. Furthermore, at least one embodiment of the invention involves the consideration to render the temperature signal of the same sensor distinguishable from the force signal of the optical force sensor in a suitable manner. As a technical means for achieving this distinction, one or more embodiments of the invention uses modulation of a measuring signal portion representing the force, in connection with a differentiated readout of this first measuring signal portion and a remaining second unmodulated measuring signal portion.

Thus, the functional principle of one or more embodiments of the invention is to be understood as follows:

From the modulation, the sensor measured value comprises a periodic portion at a frequency f, with an amplitude a, phase p, and an offset o, that change slowly over time. Via dynamic measurands of the amplitude a and the phase p, it is possible to directly determine the attenuation that is introduced into the system through external influences. Usually, during use of a catheter, this takes place when a pressing force of the tissue is applied to an oscillatory measuring head of the catheter. In contrast, the unmodulated measurand, the offset o, contains the temperature information of the sensor.

Commercially available optical Fiber Bragg strain gauges (FBG) can be read out with frequencies up to the MHz range, preferably up to 2.5 kHz. In contrast, the temperature varies in the range of just a few Hz. Accordingly, it is extremely easy to differentiate the two measurands from each other. This allows for a reliable measurement using only one sensor. This also applies to other optical strain and force sensors such as, for example, Fabry-Perot-type sensors.

At least one embodiment of the invention enables a significantly simplified solution. In terms of production, such a solution is more cost-effective than known force measuring catheter arrangements because only a single optical (FBG) sensor is required for both the force measurement and the temperature measurement. Moreover, it is conceivable that with one or more embodiments of the invention, a tissue change can be detected which was caused by a previous ablation procedure (see below). Therefore, the method discussed in one or more embodiments would also be suitable for a subsequent diagnosis, which is not possible with current methods.

At least one embodiment of the invention incorporates a resonance-tuned vibration catheter head connected to an FBG sensor in such a manner allowing the FBG sensor to measure the oscillation/vibration of the catheter head. The resonance frequency is selected such that it lies as close as possible to the modulation frequency. Furthermore, there must be sufficient thermal contact in order to determine the temperature. In order to excite the above-described oscillatory system to provide a forced oscillation, a driving excitement force is included. This introduces energy from outside into the resonance-tuned oscillation system.

In one embodiment of the invention, the above-described modulation is implemented as an amplitude modulation. In particular, this embodiment comprises a catheter with a catheter body, a distal section and a proximal section. The catheter also comprises an oscillating body mechanically connected to a force and temperature sensor, and a transmitting device to transmit the readout signal to the oscillating body and to set the oscillating body into oscillation with the carrier frequency. The oscillating body applies the carrier frequency to the force and temperature sensor while the forces acting on the distal section of the catheter represent the y-curve of the modulated measuring signal.

In one configuration, the transmitting device transmits a readout signal that includes a drive wire that extends to the proximal end of the catheter. At the proximal end of the catheter or outside of the same and still connected to the drive wire, there is an oscillation generator that sets the drive wire into oscillation. The oscillation generator, for example, is an electromechanical transducer or a piezo transducer.

In an alternative configuration, the transmitting device that transmits the readout signal includes an electrical line that extends to a connection at the proximal end of the catheter, and an electromechanical transducer or piezo transducer. In this configuration, the transducer is arranged inside the catheter body, and the drive wire provided in the previous configuration can be eliminated.

In another configuration, the transmitting device that transmits the readout signal comprises a fluid line, particularly a rinsing channel, extending to the proximal section of the catheter, and a hydraulic transducer. In this configuration, the rinsing channel is provided in the catheter body, allowing embodiments of the invention to be carried out without significant additional constructional requirements.

In a further configuration, the transmitting device that transmits the readout signal comprises an optical fiber extending up the proximal section of the catheter and an optomechanical transducer associated with the oscillating body. Laser pulses with a very short pulse duration (for example, $10^{-9}$-$10^{-15}$ seconds) enable the transmission of light pulses with a very high pulse density. The laser pulses are used to excite the resonance-tuned oscillating body to perform a forced oscillation. In this configuration, only one additional fiber is incorporated in the catheter and therefore the constructional requirements in the catheter head are minimized.

In at least one more embodiments, the excitation may also be carried out by a modulated magnetic field irradiated from the outside, wherein a force may be transmitted to a magnetic oscillatory sensor head. As in other configurations and embodiments, little to no additional components in the catheter tip are required.

Advantageous configurations of the proposed force and/or attenuation measuring device are readily apparent from the above described catheter arrangement in view of the prior art references mentioned above, and will not be repeated herein. In particular, configurations of the transmitting device to transmit the readout signal, as described above, are implemented with a catheter comprising the force and/or attenuation measuring device.

The following paragraphs further explain the configuration of the readout and processing units of the catheter arrangement or the measuring device.

In an excited periodically oscillating system, attenuation is introduced to determine the contact quality. The attenuation is derived from a decrease in amplitude as well as from a shift in phase. The attenuation has no influence on a time-averaged value of the sensor measured value from which the temperature is derived.

Moreover, two measurements are carried out under identical external conditions, with one measurement of the two carried out directly before an ablation process and the other one measurement of the two measurements carried out directly after an ablation process. From a comparison of the two measurements, and based on a potential change of the attenuation value, it is concluded that there is a tissue change that was obtained, e.g., through an ablation process. This conclusion is based on the fact that tissue that is changed by the ablation process, and in particular cicatrizes, has different properties than untreated tissue. For example, hardened tissue effects a different attenuation than comparatively soft tissue and it is therefore possible to determine if an ablation was successful. This is particularly apparent from the fact that after the ablation (with unchanged contact pressure of the distal catheter end), a changed attenuation of the oscillating system is measured.

Furthermore, another aspect arises related to ablation control. With the proposed system, one or more embodiments of the invention predict the development of bubbles, particularly air bubbles, during the ablation. Preferably, these air bubbles are to be avoided. It is found that shortly before the development of these bubbles, vibrations develop in the catheter that are detected with the elements disclosed in one or more embodiments of the invention.

BRIEF DESCRIPTION OF THE DRAWINGS

The invention will now be described in more detail hereafter by way of example based on exemplary embodiments with reference to the figures, wherein.

DETAILED DESCRIPTION OF THE INVENTION

Figure 1:
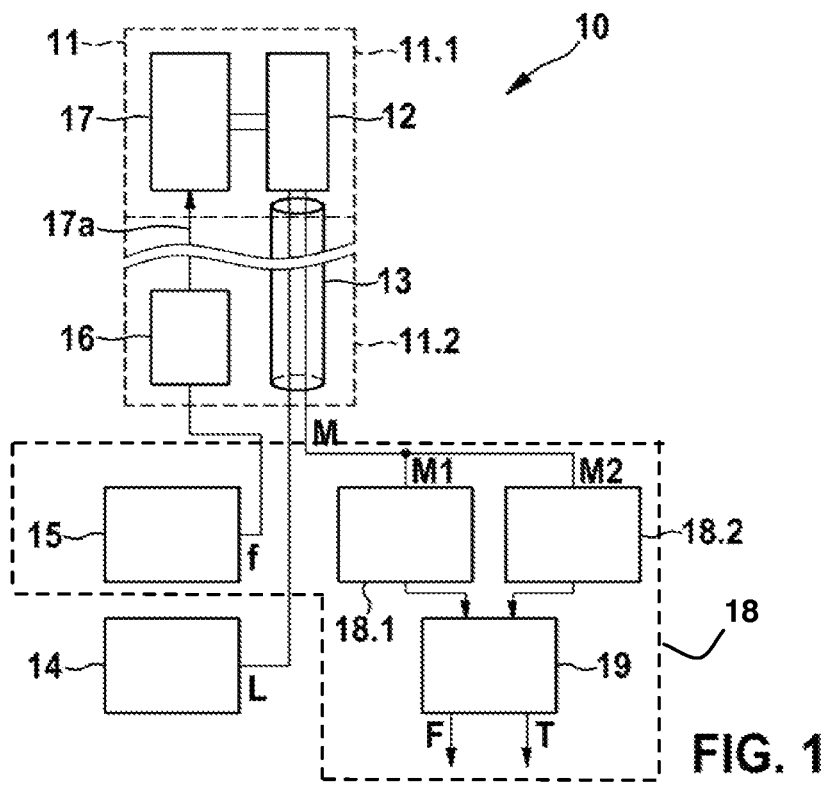
FIG. 1: shows a schematic illustration of an embodiment of the catheter arrangement.

FIG. 1 shows elements of a catheter arrangement 10 that are in accordance with at least one embodiment of the invention. The catheter arrangement comprises an ablation catheter 11 with a distal section and a proximal section, a catheter head 11.1 and a catheter body 11.2. In the catheter head 11.1, an optical force and temperature sensor 12 is connected to an optical fiber 13 that extends up to the proximal section of the catheter body 11.2. An excitation light source 14 generates and emits measuring light L via the optical fiber 13 into the optical sensor 12. Furthermore, from the optical fiber 13, a measuring signal M is modulated according to a state of strain, and is received at an evaluation unit 18 according to a force acting on the optical sensor.

A carrier frequency generator (readout signal generator) 15 generates an electric oscillation f, for example of some hundred Hz, and is transduced via an electromechanical transducer 16 at the proximal section of the catheter body 11.2 into a mechanical oscillation. The mechanical oscillation is transmitted via a drive wire 17a that extends up to the catheter head and to an oscillating body 17 in the catheter head 11.1. The oscillating body is mechanically coupled to the optical sensor 12 and transmits its oscillations to the optical sensor in order to modulate a readout signal with the frequency f.

This modulated readout signal effects the measuring signal M, and comprises two components: a first component M1 modulated with the carrier frequency f and unmodulated second component M2. In this manner, the time domain of the carrier frequency is considered as being stationary). The measuring signal portions M1, M2 are received at first and the second readout devices 18.1 and 18.2, respectively. The first and second readout devices read out the measuring signal portions M1 and M2. After the first and second read out devices, the measuring signal portions are received at a processing unit 19 that combines the first and second signal portions M1 and M2, and respectively extracts an exclusively force-dependent or attenuation-dependent component F and an exclusively temperature-dependent component T.

Figure 2:
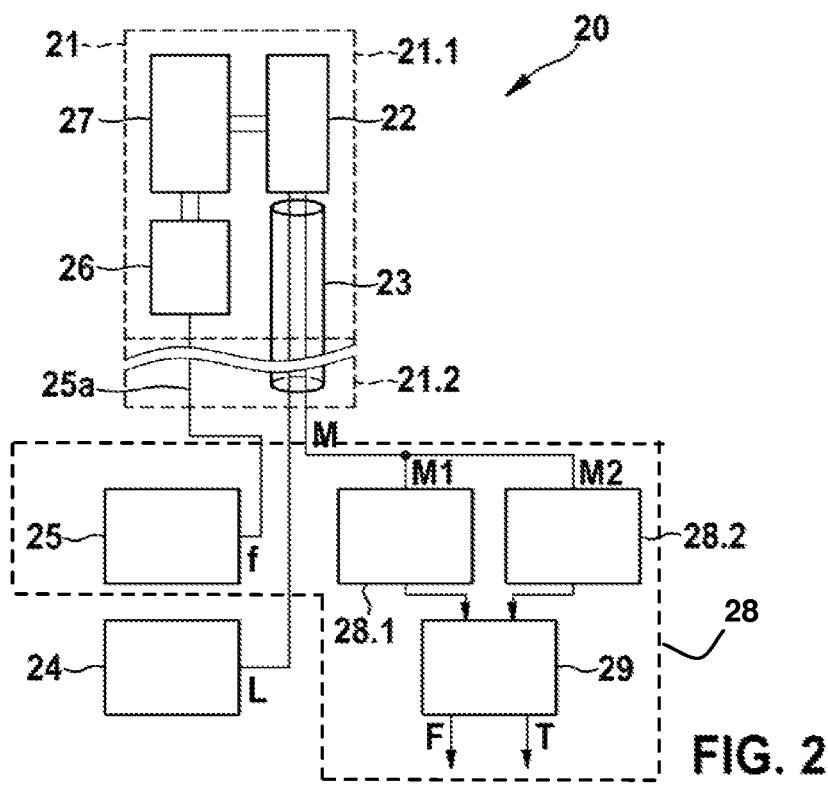
FIG. 2: shows a schematic illustration of a further embodiment of the catheter arrangement.

A modified catheter arrangement 20 according to FIG. 2 has largely the same structure as the above-described catheter arrangement 10, therefore the reference numbers based on FIG. 1 are used in describing FIG. 2, and the common elements previously described are not described again. Accordingly to FIG. 2, the essential difference between catheter arrangement 20 and the catheter arrangement 10 is that the carrier frequency f is transmitted by a carrier frequency generator 25 via an electrical line connection 25a and into the catheter head. Via a piezo transducer 26, and only in the catheter head, the carrier frequency is then transduced into a mechanical oscillation. By directly mechanically coupling the piezo transducer 26 to the oscillating body 27, the oscillation is transmitted to the oscillating body.

Figure 3:
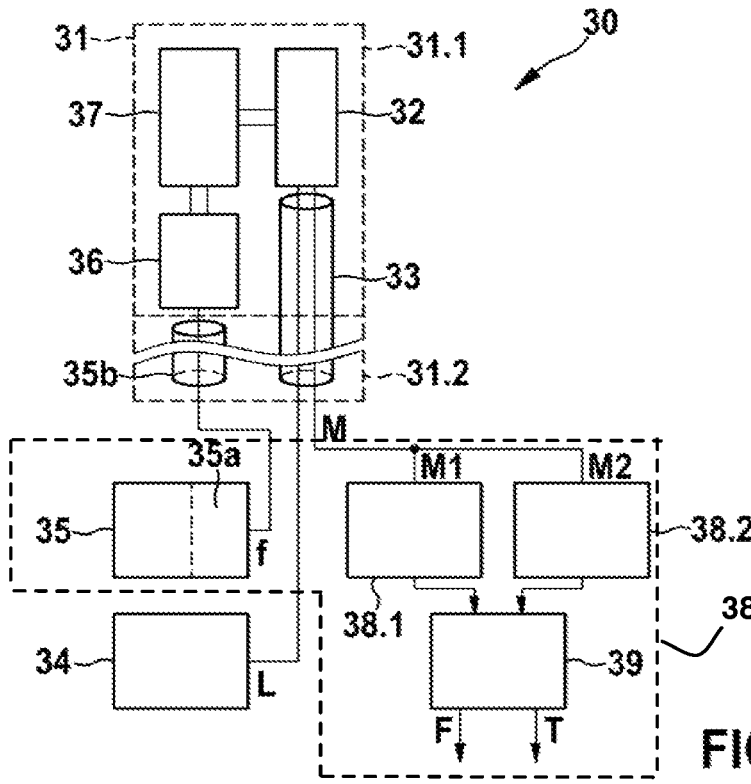
FIG. 3: shows a schematic illustration of a further embodiment of the catheter arrangement.

The catheter arrangement 30 shown in FIG. 3 is also similar to the two aforementioned catheter arrangements 10 and 20, therefore the reference numbers based on FIGS. 1 and 2 are used and the corresponding components—in particular the reference number of the elements for generating and transmitting the excitation light and for transmitting and evaluating the measuring signal—are not explained again. According to FIG. 3, the essential difference between the catheter arrangement 30 and the previously described catheter arrangements 10, 20 is that the carrier frequency generator 35 has an optical output 35a, in which an output signal from the optical output is connected into an optical fiber that extends from the proximal section of the catheter body 31.2 to the catheter head 31.1. An optomechanical transducer 36 is located in the catheter head 31.1 that is mechanically and directly coupled to oscillating body 37. The optomechanical transducer 35 transduces the frequency f into a mechanical oscillation, and transmits the frequency f transduced into a mechanical oscillation directly to the oscillating body 37.

Figure 4:
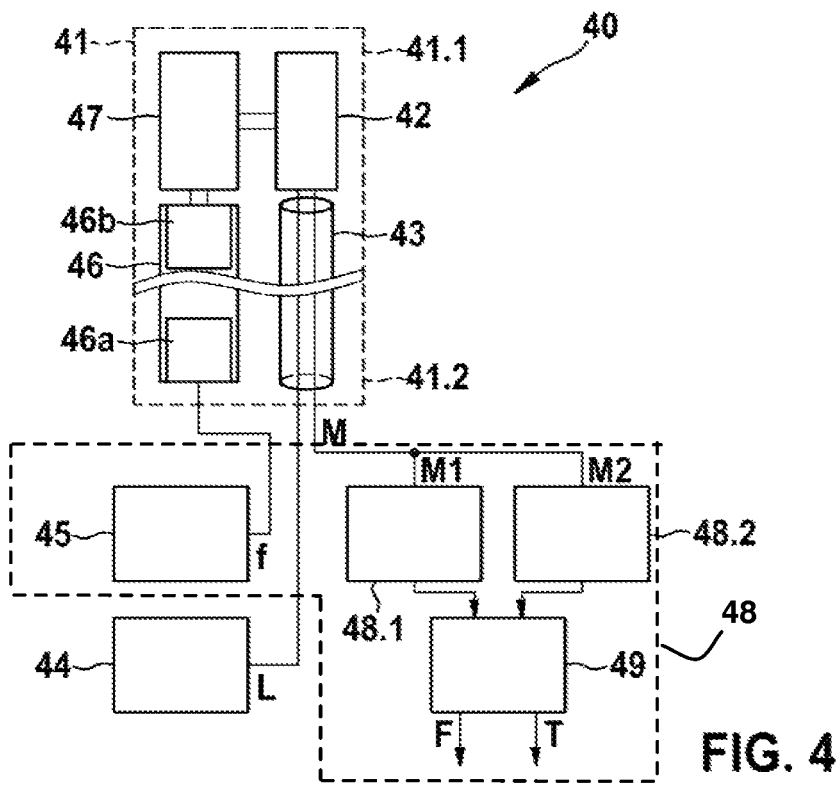
FIG. 4: shows a schematic illustration of a further embodiment of the catheter arrangement.
Figure 5A:
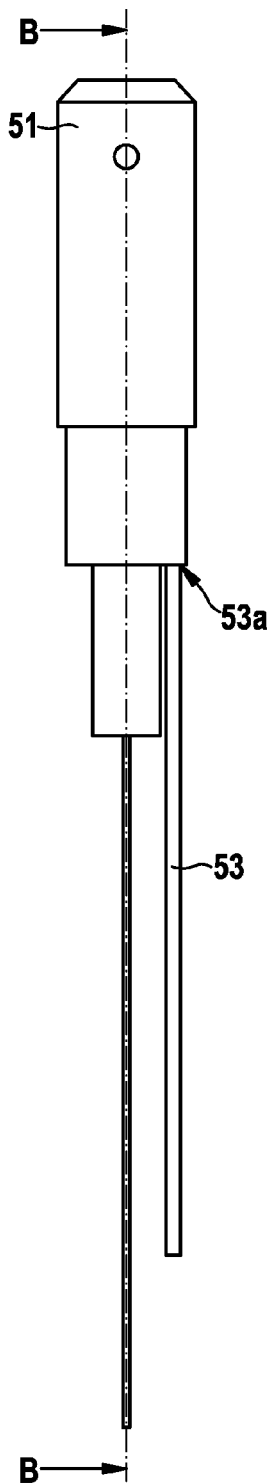
FIGS. 5A to 5D: show different illustrations of components in the distal region of the catheter of a further embodiment of the catheter arrangement.
Figure 5B:
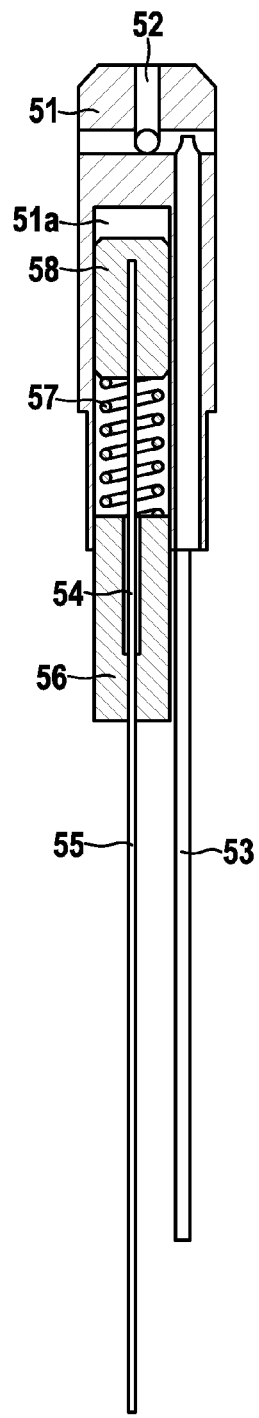
Figure 5C:
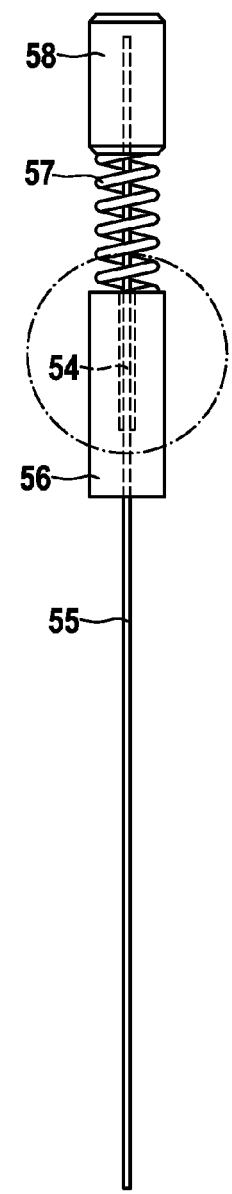
Figure 5D:
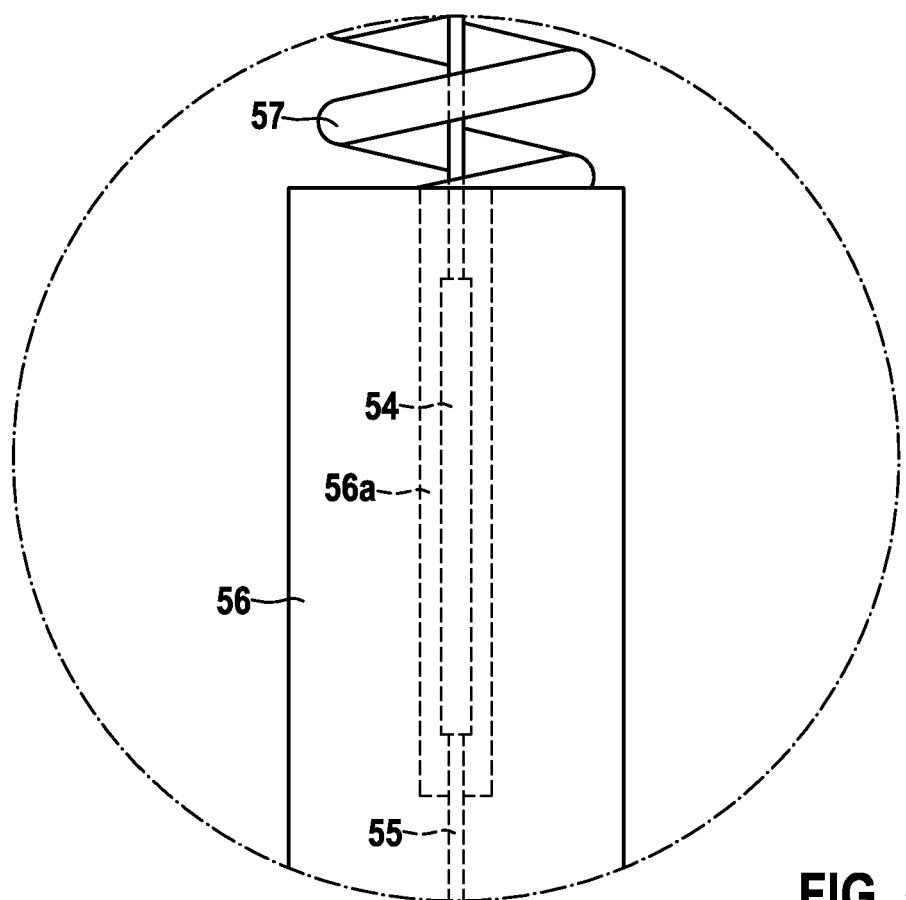

According to FIG. 4, the only difference between the catheter arrangement shown in FIG. 4 and the catheter arrangements previously described, in accordance with FIGS. 1-3, is the transmission of the readout or carrier frequency f to the oscillating body 47. Looking at FIG. 4, the transmission is carried out hydraulically through a liquid column in a rinsing channel of an electrohydraulic transducer 46. At the distal section of a catheter 41, the electrohydraulic transducer 46 is assigned to, connected to and associated with the rinsing channel, and at a distal channel end, a hydraulic transducer or closure member 46b is mechanically coupled to the oscillating body 47 and is assigned to, connected to and associated with the rinsing channel. In order to drive the oscillating body 47, a liquid column is used, specifically via a rinsing liquid in the rinsing channel that is located in the catheter 41.

FIGS. 5A to 5D show ablation catheter elements essential for the one or more embodiments of the invention. FIG. 5A-5D show a catheter head 51 that has a rinsing channel arrangement 52, a plurality of outlets located on a tip of the catheter and on a circumference close to a distal end of the catheter, and a pull wire 53 fastened at a fastening point (welding spots, etc.) to the catheter head 51.

Inside the catheter head, a force or attenuation measuring device, specifically a FBG strain measuring device 54, is located. Measuring device 54 has a connected glass fiber 55 for transmitting an excitation signal into an FBG sensor, for transmitting a tapped measuring signal to a proximal section of the catheter and to an evaluation device. An oscillating body 58 is attached via a spring element 57 to a sensor housing 56. The oscillating body, spring element and sensor housing are all together located in a cylindrical bore 51a of the catheter head. A heat conducting paste, optionally provided around the FBG grating 54 in the respective channel 56a of the sensor housing 56, improves thermal contact between the catheter head (and therefore the tissue surrounding the catheter head) and the grating, and therefore improves the grating's response characteristic and precision in its function as a T sensor.

According to the above explanations of the construction of different embodiments of the proposed catheter arrangement, the catheter head of the respective catheter is designed as an oscillatory system and as an optical sensor system. The catheter head comprises a FBG sensor element and a connected optical fiber that measure and analyze the oscillation forced onto said sensor system.

Oscillatory excitation is introduced into the system, for example, via a pull wire, via an acoustic signal in a rinsing hose, via an electrical signal in connection with a piezo element or an electromagnetic element, via an optical pulse or via an external force such as, for example, an external magnetic field. The aim of the excitation is to set the catheter head into oscillation. When the catheter head outputs an oscillating movement, the oscillating body that is connected to the catheter head via a spring element, is also set into oscillation.

The Fiber Bragg sensor measures a relative movement between the catheter head and the oscillation body. The measurands are the amplitude of the movement and the phase relative to the excitation oscillation. Once the catheter head comes into contact with the surrounding tissue, an additional attenuation is introduced into the system that influences the amplitude and the phase of the oscillation. Therefore from the measurands, the attenuation and hence the contact quality of the catheter head to the surrounding tissue is determined.

During a temperature change, the system expands corresponding to the thermal expansion coefficient of the materials used. This expansion results in a length change. Thereby, the grating spacing of the Fiber Bragg Grating changes, resulting in a spectral shift of its reflection properties. From this, the temperature can be determined.

At the same time, if the system outputs an oscillation, the deflection of said oscillation is symmetrical to a zero position. A measured value that corresponds to the zero position corresponds exactly to a measured temperature value. By determining a time-averaged value, the zero position (and therefore the temperature) can be determined, since the deflection of the oscillation is always symmetrical relative to the zero position. The time-averaged value of the FBG sensor therefore represents the temperature.

The excitation or the measuring method is carried out in a time domain or in a frequency domain:

Time Domain:

In one configuration of the measuring method, short excitation pulses are introduced into the system with a repetition rate that is significantly higher than the natural frequency of the oscillating system. Thereby, a time-related decay behavior of an amplitude decrease can be determined after an excitation by the pulse is produced. An attenuation constant results directly from the time constant that characterizes this decrease.

Frequency Domain:

In a second configuration, the system is continuously set into oscillation with a constant excitation amplitude using harmonic excitation at approximately the natural frequency of the oscillating system. The amplitude and the phase that arise without external influence on the system can easily be determined, for example during a reference measurement outside of the body and/or the inside the body. However this occurs at a time at which no contact pressure is applied to the tissue. Once the catheter is brought into contact with the tissue, the system is attenuated and an amplitude decrease and a phase shift between the excitation oscillation and the oscillation system can be measured. As a result, the attenuation is directly determined.

In addition, in the second configuration, measuring filters such as lock-in amplifiers that have extremely high measuring sensitivity are used. In doing so, the excitation signal would be applied as a reference signal to the lock-in amplifier, and the measuring signal coming from the FBG sensor would be applied to the input of the lock-in amplifier. The lock-in amplifier then multiplies the input signal by its reference signal and integrates the result over a certain time interval, wherein all frequencies are filtered, except for the excitation frequency. This allows for an extremely good signal-to-noise ratio. The value of the measured amplitude of the FBG sensor as well as the phase relative to the excitation oscillation is then directly obtained as an output value.

The implementation of the invention is not limited to the above-described examples and emphasized aspects, but is also possible in a multiplicity of modifications that are apparent to those skilled in the art.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A catheter arrangement comprising:
    an ablation catheter with a distal section and a proximal section;
    wherein said ablation catheter comprises
        a single combined optical force and temperature sensor integrated with said distal section and configured to measure a force acting on said distal section, and simultaneously receive a temperature signal prevailing in said distal section; and
    an evaluation unit connected to said optical force and temperature sensor,
        wherein said evaluation unit comprises
            a readout signal generator configured to generate and feed a readout signal modulated with a carrier frequency into said optical force and temperature sensor,
            a first readout device configured to read out a first modulated measuring signal portion (M1) modulated with said carrier frequency,
            a second readout device configured to read out a second unmodulated measuring signal portion (M2), and
            a processing unit configured to
                combine said first modulated measuring signal portion and said second unmodulated measuring signal portion, and
                determine an exclusively force-dependent or attenuation-dependent component and an exclusively temperature-dependent component for said first modulated measuring signal portion and said second unmodulated measuring signal portion respectively.

2. The catheter arrangement according to claim 1, wherein said ablation catheter further comprises:
    an oscillating body mechanically connected to said optical force and temperature sensor, and
    a transmitting device configured to
        transmit said readout signal to said oscillating body, and set said oscillating body into oscillations with said carrier frequency.

3. The catheter arrangement according to claim 2, wherein said transmitting device comprises a drive wire that extends to said proximal section.

4. The catheter arrangement according to claim 2, wherein said proximal section comprises a connection, and wherein said transmitting device comprises
    an electrical line that extends to said connection, and
    an electromechanical or piezo transducer.

5. The catheter arrangement according to claim 2, wherein said transmitting device comprises
    a liquid line or a irrigation channel that extends to said proximal section, and
    a hydraulic transducer.

6. The catheter arrangement according to claim 2, wherein said transmitting device comprises
    an optical fiber that extends to said proximal section, and
    an opto-mechanical transducer directly associated with said oscillating body.

7. The catheter arrangement according to claim 1, wherein said force and temperature sensor is a Fiber-Bragg-Grating-type (FBG type) sensor or Fabry-Perot-type sensor.

8. A measuring device for at least one force and attenuation measurements, comprising:
    a single combined optical force and temperature sensor;
    an input element configured to feed a readout signal modulated with a carrier frequency into said optical force and temperature sensor;
    and,
    an output element coupled to said optical force and temperature sensor, wherein said output element is configured to output a measuring signal; wherein said measuring signal comprises
        a first modulated measuring signal portion (M1) modulated with said carrier frequency, and
        a second unmodulated measuring signal portion (M2).

9. The measuring device according to claim 8, wherein said optical force and temperature sensor is a FBG-type sensor or Fabry-Perot-type sensor.

10. The measuring device according to claim 8, further comprising
an oscillating body; and
a transmitting device configured to
transmit said readout signal to said oscillating body, and
set said oscillating body into oscillations with said carrier frequency;
wherein said oscillating body and said transmitting device are directly associated with said optical force and temperature sensor.

11. A catheter comprising:
a proximal section and a distal section; and,
a measuring device configured to measure at least one of force measurements and attenuation measurements, comprising:
a single combined optical force and temperature sensor;
an input element configured to feed a readout signal modulated with a carrier frequency into said optical force and temperature sensor; and,
an output element coupled to said optical force and temperature sensor, wherein said output element is configured to output a measuring signal, wherein said measuring signal comprises
a first modulated measuring signal portion (M1) modulated with said carrier frequency, and
a second unmodulated measuring signal portion (M2).

12. The catheter according to claim 11, wherein said catheter is an ablation catheter.

13. The catheter according to claim 11, further comprising a transmitting device, wherein said transmitting device comprises a drive wire that extends to said proximal section.

14. The catheter according to claim 11, wherein said proximal section comprises a connection.

15. The catheter according to claim 14, further comprising a transmitting device and an oscillating body;
wherein said transmitting device comprises
an electrical line that extends to said connection, and
an electromechanical or piezo transducer directly associated with said oscillating body.

16. The catheter according to claim 11, further comprising a transmitting device configured to transmit said readout signal, wherein said transmitting device comprises
an irrigation liquid line or an irrigation liquid line that extends to said proximal section and
a hydraulic transducer directly associated with said oscillating body.

17. The catheter according to claim 11, further comprising a transmitting device configured to transmit said readout signal, wherein said transmitting device comprises
an optical fiber that extends to said proximal section, and
an optomechanical transducer directly associated with said oscillating body.

* * * * *